US007731697B2

(12) United States Patent
Porter et al.

(10) Patent No.: US 7,731,697 B2
(45) Date of Patent: Jun. 8, 2010

(54) APPARATUS AND METHOD FOR PERCUTANEOUS CATHETER IMPLANTATION AND REPLACEMENT

(75) Inventors: Christopher H. Porter, Woodinville, WA (US); Claude A. Vidal, Santa Barbara, CA (US); Russ J Redmond, Goleta, CA (US); Byron L. Moran, Santa Barbara, CA (US); Paul Kaluzniak, Simi Valley, CA (US); Abram D. Janis, Valencia, CA (US)

(73) Assignee: Incumed LLC, A Nevada Limited Liability Co., Valencia, CA (US)

( * ) Notice: Subject to any disclaimer, the term of this patent is extended or adjusted under 35 U.S.C. 154(b) by 405 days.

(21) Appl. No.: 11/708,445

(22) Filed: Feb. 20, 2007

(65) Prior Publication Data
US 2007/0149949 A1    Jun. 28, 2007

Related U.S. Application Data

(63) Continuation-in-part of application No. 10/821,383, filed on Apr. 9, 2004, now Pat. No. 7,604,617.

(60) Provisional application No. 60/462,265, filed on Apr. 12, 2003.

(51) Int. Cl.
*A61M 5/32* (2006.01)
(52) U.S. Cl. .................................. 604/175; 604/174
(58) Field of Classification Search .............. 604/93.01, 604/174, 175, 264, 43, 164.01, 523, 533; 206/571
See application file for complete search history.

(56) References Cited

U.S. PATENT DOCUMENTS 3,157,277 A * 11/1964 Sorenson .................... 206/365

(Continued)

FOREIGN PATENT DOCUMENTS

EP        0 367 354 B1    2/1993

(Continued)

OTHER PUBLICATIONS

Jensen, J.A. Tissue reaction to soft-tissue anchored percutaneous Implants in rabbits Journal of Biomedical Medical Research, 1994 vol. 28, pp. 1047-1054.

(Continued)

*Primary Examiner*—Nicholas D Lucchesi
*Assistant Examiner*—Christopher D Koharski
(74) *Attorney, Agent, or Firm*—Freilich, Hornbaker & Rosen (57) ABSTRACT

A medical apparatus and method of use for implanting a catheter in a patient's body which catheter can be easily positioned, repositioned, and replaced. The apparatus includes an elongate sleeve comprising a wall surrounding an interior passageway extending from a sleeve proximal end to a sleeve distal end. The sleeve is intended to be percutaneously implanted through an incision in the patient's skin to place the sleeve distal end subcutaneously. The sleeve distal end outer surface carries porous material intended to contact the patient's dermis to promote tissue ingrowth. The sleeve passageway is dimensioned to snugly accommodate the outer surface of the catheter while permitting the catheter to slide relative to the sleeve. A split ring locking member is selectively operable in an unlocked state for permitting axial and rotational movement of said catheter relative to said sleeve and operable in a locked state for preventing such relative movement.

18 Claims, 6 Drawing Sheets

U.S. PATENT DOCUMENTS

| | | | |
|---|---|---|---|
| 3,447,161 A | 6/1969 | Weikel | |
| 3,683,911 A | 8/1972 | McCormick | |
| 3,783,868 A | 1/1974 | Bokros | |
| 4,278,092 A | 7/1981 | Borsanyi et al. | |
| 4,417,888 A | 11/1983 | Cosentino et al. | |
| 4,488,877 A | 12/1984 | Klein et al. | |
| 4,496,349 A | 1/1985 | Cosentino | |
| 4,540,411 A | 9/1985 | Bodicky | |
| 4,592,749 A | 6/1986 | Ebling et al. | |
| 4,648,391 A | 3/1987 | Ellis | |
| 4,668,222 A | 5/1987 | Poirier et al. | |
| 4,728,331 A | 3/1988 | Russier | |
| 4,729,366 A | 3/1988 | Schaefer | |
| 4,781,693 A | 11/1988 | Martinez et al. | |
| 4,781,694 A | 11/1988 | Branemark et al. | |
| 4,886,502 A | 12/1989 | Poirier et al. | |
| 4,897,081 A | 1/1990 | Poirier et al. | |
| 5,007,897 A | 4/1991 | Kalb et al. | |
| 5,041,085 A | 8/1991 | Osborne et al. | |
| 5,085,646 A | 2/1992 | Svenson et al. | |
| 5,098,434 A | 3/1992 | Serbousek | |
| 5,221,263 A | 6/1993 | Sinko et al. | |
| 5,318,040 A | 6/1994 | Kensey et al. | |
| 5,360,397 A | 11/1994 | Pinchuk | |
| 5,383,863 A * | 1/1995 | Mardones | 604/198 |
| 5,411,467 A | 5/1995 | Hortmann et al. | |
| 5,715,815 A | 2/1998 | Lorenzen et al. | |
| 5,885,217 A | 3/1999 | Gisselberg et al. | |
| 5,931,838 A | 8/1999 | Vito | |
| 6,099,508 A | 8/2000 | Bousquet | |
| 6,156,016 A * | 12/2000 | Maginot | 604/264 |
| 6,332,874 B1 | 12/2001 | Eliasen et al. | |
| 6,520,939 B2 | 2/2003 | LaFointaine | |
| 6,638,253 B2 * | 10/2003 | Breznock | 604/164.04 |
| 6,916,310 B2 | 7/2005 | Sommerich | |
| 6,955,677 B2 | 10/2005 | Dahners | |
| 2002/0072712 A1 | 6/2002 | Nool et al. | |
| 2002/0107475 A1 | 8/2002 | Maginot | |
| 2003/0149422 A1 | 8/2003 | Muller | |
| 2003/0199827 A1 | 10/2003 | Thorne | |
| 2004/0204686 A1 | 10/2004 | Porter et al. | |
| 2005/0059925 A1 | 3/2005 | Maginot et al. | |
| 2006/0030817 A1 | 2/2006 | Kraus et al. | |
| 2008/0108969 A1 | 5/2008 | Kerr | |

FOREIGN PATENT DOCUMENTS

GB     2268066 A     1/1994

OTHER PUBLICATIONS

Bandyopadhyay, Balaji et al., A "traffic control" role for TGFb3: orchestrating dermal and epidermal cell motility during wound healing Journal of Cell Biology, Mar. 27, 2006, vol. 172, No. 7, pp. 1093-1105.

* cited by examiner

APPARATUS AND METHOD FOR PERCUTANEOUS CATHETER IMPLANTATION AND REPLACEMENT

RELATED APPLICATIONS

This application is a continuation-in-part of U.S. application Ser. No. 10/821,383 filed on Apr. 9, 2004 now U.S. Pat. No. 7,604,617, which claims priority based on U.S. Provisional Application 60/462,265 filed on Apr. 12, 2003. This application claims priority based on both of said applications and, in addition, on U.S. Provisional Application 60/758,137 filed on Jan. 11, 2006. The aforementioned applications are, by reference, incorporated herein.

FIELD OF THE INVENTION

This invention relates generally to medical technology and more particularly to a method and apparatus for implanting an elongate conduit, e.g., a catheter or cable, so as to extend through a patient's skin for providing long term access to an interior body site. Embodiments of the invention are useful in a variety of applications, e.g., in hemodialysis procedures to enable a catheter to provide fluid access to a patient's central venous system and/or nerve stimulation procedures in which a cable provides access to an implanted electric device.

BACKGROUND OF THE INVENTION

In a variety of medical procedures, catheters are implanted through a patient's skin to provide long term access to interior body sites; e.g., blood vessels and organs. Unless adequate precautions are taken, infections and inflammation can readily occur at the catheter entry site. To mitigate such problems, a tissue integrating cuff is sometimes attached to the catheter and placed under the patient's skin to resist infection. Although such a cuff can reduce the likelihood of infection, its presence increases the difficulty of removing and/or repositioning an implanted catheter. More particularly, it is not uncommon for an implanted catheter to become damaged, e.g., clogged or kinked, over an extended period of use thus necessitating catheter removal and/or replacement. When this occurs, the cuff must be dissected thereby complicating and prolonging the surgical procedure.

The aforementioned application Ser. No. 10/821,383 describes the use of a tissue integrating structure on a percutaneously implanted medical device for anchoring the device and creating an infection resistant barrier around the device.

SUMMARY OF THE INVENTION

The present invention is directed to a medical apparatus and method of use for percutaneously implanting an elongate conduit, e.g., a catheter or cable, in a patient's body in a manner which allows the conduit to be easily positioned, repositioned, and replaced.

An apparatus in accordance with the invention includes an elongate sleeve comprising a wall surrounding an interior elongate passageway. The passageway extends from a sleeve proximal end to a sleeve distal end. The sleeve is intended to be percutaneously implanted through an incision in the patient's skin so that the sleeve distal end resides beneath the skin, i.e., subcutaneously, and the sleeve proximal end resides above the skin. The sleeve outer peripheral surface carries a layer of porous material, e.g., a biocompatible mesh, as described in U.S. application Ser. No. 10/821,383, intended to be placed just under the patient's outer skin layer in contact with the dermis to promote tissue ingrowth for anchoring the sleeve and forming an infection resistant barrier. The sleeve passageway is dimensioned to snugly accommodate the outer surface of a conduit (which will hereinafter be assumed to be a catheter unless otherwise stated) while permitting the conduit to slide and rotate in the passageway relative to the sleeve. A sealing device within the sleeve extends around the catheter, e.g., near the sleeve proximal end, to prevent deleterious material from migrating into the patient's body along the catheter outer surface.

In one preferred embodiment, the sealing device comprises an annular seal formed of a soft flexible material, e.g., silicone, mounted within the passageway of an elongate rigid sleeve formed, for example, of titanium. The annular seal comprises a peripheral wall having an outer surface and an inner surface surrounding an interior bore. At least one annular flexible nib on the annular seal inner surface projects radially into the bore for sealing against the catheter outer surface. Alternatively, the sleeve can be formed of flexible polymer tubing, e.g., silicone, allowing an interior annular sealing nib to be formed integral therewith.

A preferred embodiment also includes a locking member mounted at the sleeve proximal end. The locking member is configured so it can be readily manipulated by a physician to selectively define either a first, or unlocked, state, and a second, or locked, state. In the unlocked state, the conduit (e.g., catheter) is able to slide and/or rotate relative to the sleeve passageway. In the locked state, a friction force is applied to the catheter to prevent relative movement between the catheter and the sleeve.

A preferred locking member comprises a split ring formed of a soft flexible material, e.g., silicone, surrounding the catheter and dimensioned such that its interior bore in said unlocked state is sufficiently large to avoid restricting catheter movement. In the locked state, the split ring is radially compressed to frictionally grip the catheter outer surface to prevent catheter movement relative to the sleeve. The split ring can be compressed in various ways; e.g., by simply tying it with suture thread or by using an internal or external clip, e.g., spring urged clamp, to pinch the split ring.

In typical use, a physician will make an incision proximate to the patient's chest or abdomen. A surgical tunneler tool is then typically inserted through the incision to form a subcutaneous tunnel to an interior site through which a standard flexible catheter can be inserted. In accordance with the invention, the catheter carries the aforementioned sleeve, annular seal, and locking member. The distal end of the sleeve is then inserted through the incision to locate the sleeve porous layer in contact with the dermis just below the patient's outer skin surface. The sleeve proximal end may, at the physician's option, be externally anchored to the patient's skin. With the locking member in its unlocked state, the physician is able to slide and/or rotate the catheter relative to the sleeve and locking member for optimum catheter positioning. When the catheter is properly positioned, the physician can then manipulate the locking member to the locked state to lock the catheter relative to the sleeve. With the sleeve thus implanted, the patient's subcutaneous tissue will, over time, grow into the porous material to anchor the sleeve and form an infection resistant barrier. The porous material, and/or sleeve interior, can be coated or impregnated with constituents having antimicrobial and/or anti-inflammatory properties to promote healing, e.g., silver containing compounds or antibiotic eluting coatings and/or steroids.

In one preferred embodiment of the invention, a sheath of thin flexible material is mounted around the sleeve and porous layer prior to use to avoid tissue damage to the patient as the sleeve porous layer is inserted through the incision. The sheath is preferably configured with a projecting tab which allows the physician to readily peel the sheath away, e. g, with one hand, as the sleeve is being implanted. The sheath preferably includes a preformed score or perforation line which can be readily fractured by the physician as he/she manipulates the tab after the sleeve has been inserted through the incision.

After the sleeve and catheter have been implanted, subcutaneous tissue will gradually grow into the porous layer to form an infection resistant barrier around the sleeve to prevent fluid and/or other deleterious material from migrating into the body along the sleeve outer surface. The annular seal functions to prevent deleterious material from migrating into the body along the catheter outer surface. A catheter assembly in accordance with the invention enables the physician at some later date (e.g., months) to replace the implanted catheter while leaving the sleeve in place. To do this, the physician will typically insert a temporary guide wire through the old catheter and then unlock the locking member to allow the old catheter to be withdrawn along the guide wire from the sleeve proximal end. A new catheter is then slid over the guide wire through the implanted sleeve, seal, and locking member. After the new catheter is properly positioned, the physician can then lock the new catheter in place by manipulating the locking member.

DETAILED DESCRIPTION

Various medical regimens relating, for example, to hemodialysis drug infusion, plasmapheresis, etc., use a percutaneously implanted conduit for conveying fluid and/or electric signals to/from an interior body site. The present invention is directed to a method and apparatus for facilitating the implantation and utilization of a percutaneous conduit (e.g., catheter) and for facilitating the positioning, repositioning, and replacement, or exchange, of the catheter.

Figure 1:
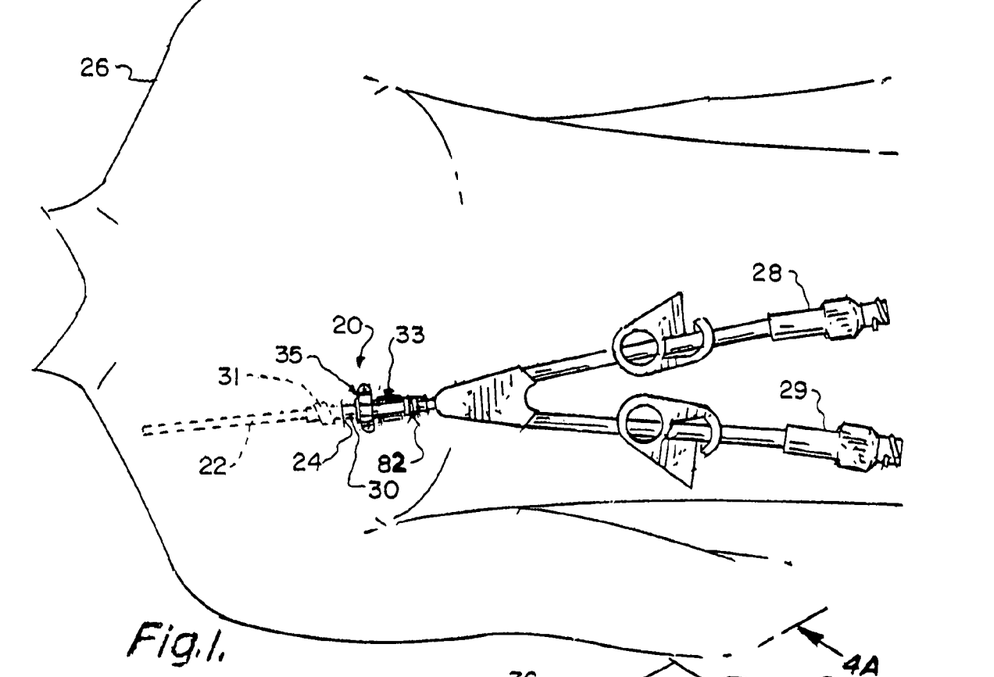
FIG. 1 is a schematic representation generally depicting a catheter assembly in accordance with the invention for percutaneously implanting a catheter for an exemplary hemodialysis application.

FIG. 1 schematically depicts an assembly 20 in accordance with the invention for percutaneously implanting a catheter 22 through an incision 24 in a patient 26 undergoing an exemplary hemodialysis procedure. In such a procedure, a dual lumen catheter 22 is typically used with the two lumens being respectively coupled to separate exterior flow couplers 28 and 29.

Figure 2:
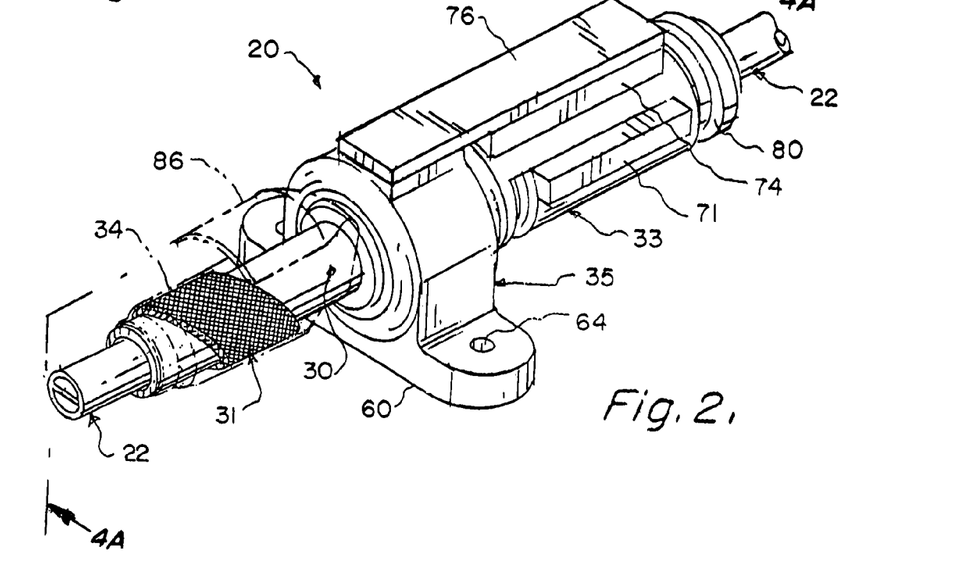
FIG. 2 is an isometric view of a preferred catheter assembly in accordance with the invention.
Figure 3:
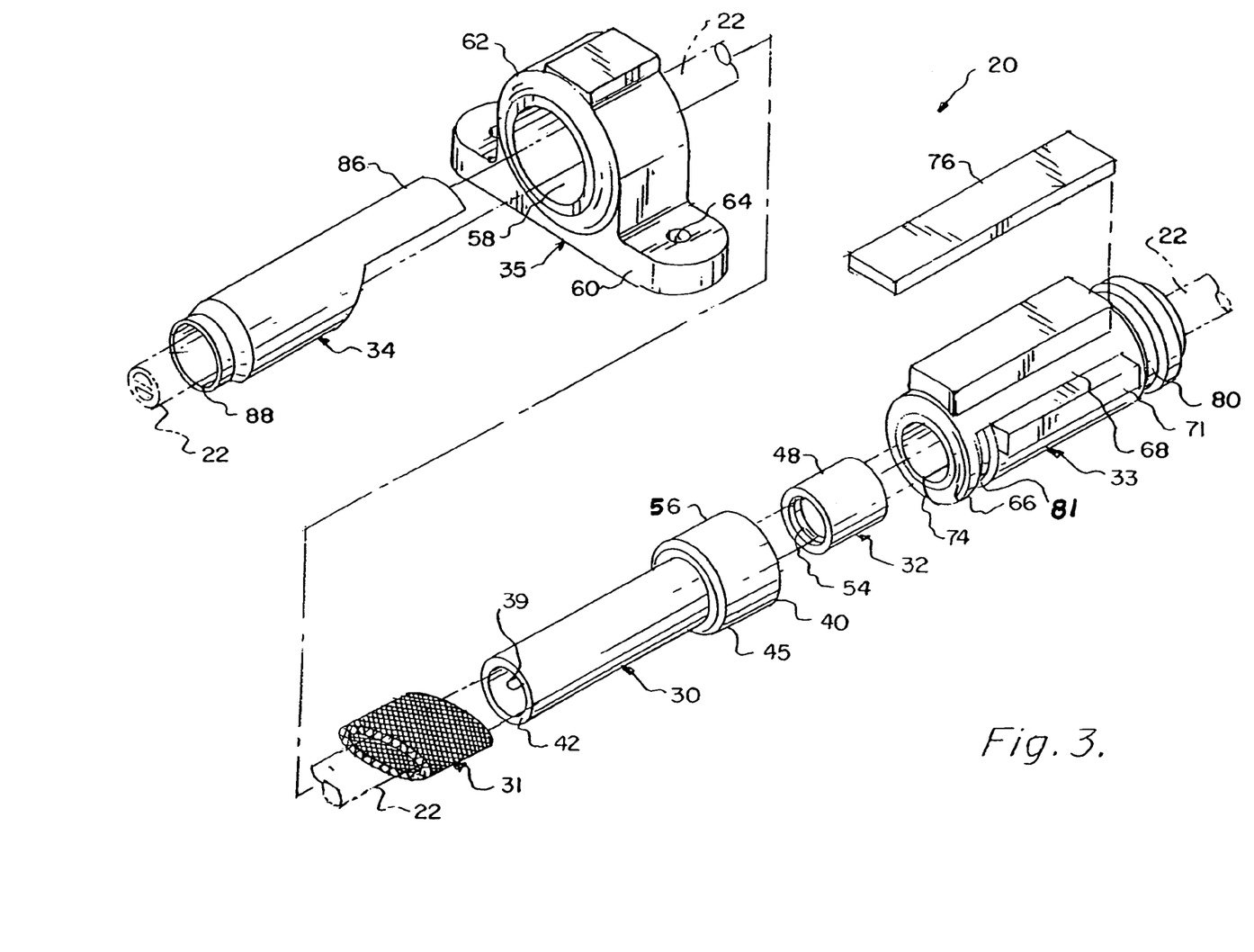
FIG. 3 is an exploded view of the assembly of FIG. 2 showing a catheter in phantom together with a protective sheath, an anchor, a sleeve carrying a of porous material, an annular seal, and a locking member.
Figures 4A, 4B, 4C, 4D, 4E:
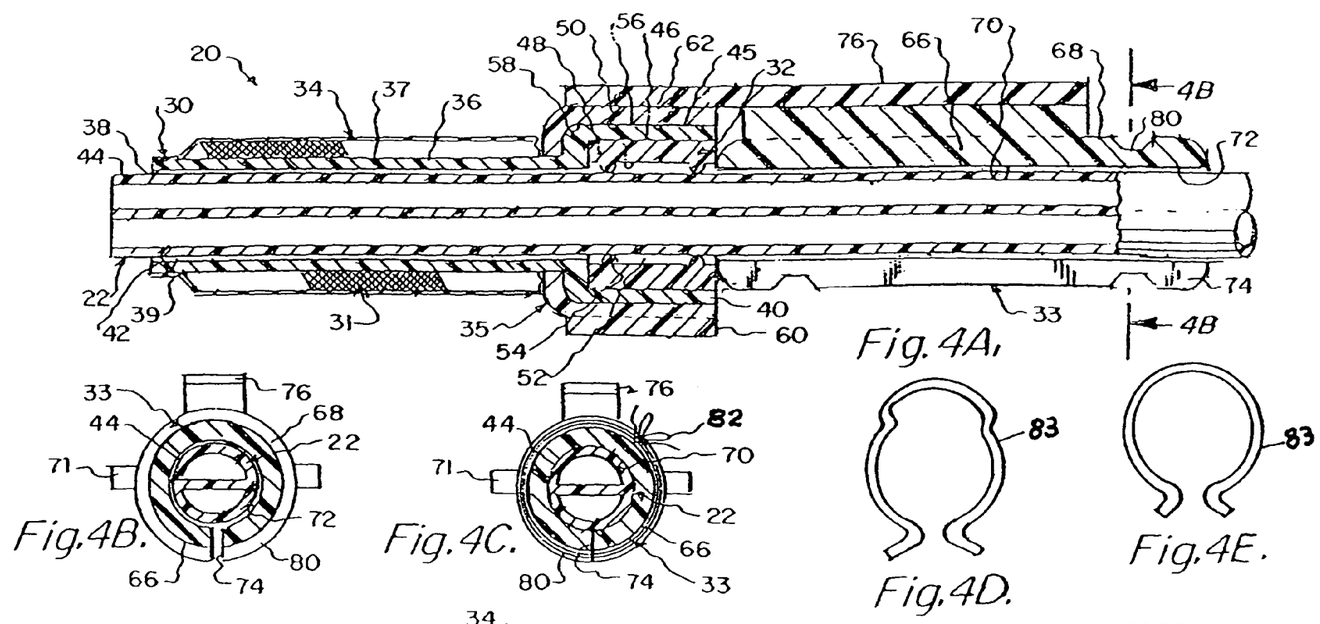
FIG. 4A is a sectional view taken substantially along the plane 4A-4A of FIG. 2.
FIG. 4B is a sectional view taken substantially along the plane 4B-4B of FIG. 4A showing the locking member in its unlocked state.
FIG. 4C is a sectional view similar to FIG. 4B showing the locking member in its locked state clamped by suture wire.
FIGS. 4D and 4E show exemplary spring clips which can be alternatively used for clamping the locking member in its locked state.
Figure 5:
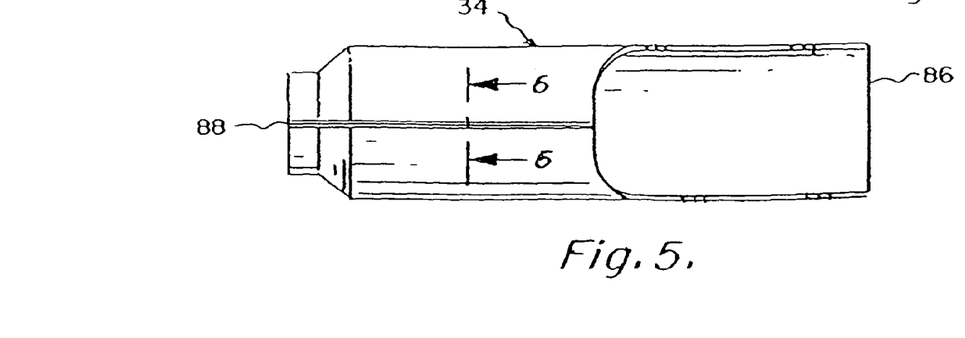
FIG. 5 is a plan view of the protective sheath of FIG. 3.
Figure 6:
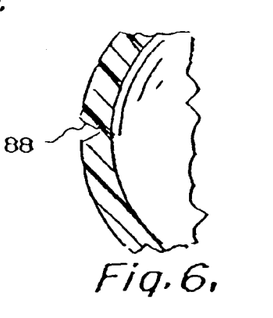
FIG. 6 is a sectional view taken substantially along the plane 6-6 of FIG. 5 particularly showing a preformed score line.

Attention is now directed to FIGS. 2-4 which depict a preferred catheter assembly 20 in accordance with the present invention. FIG. 3 best shows the primary elements of the assembly 20 including sleeve 30 carrying a porous layer 31, a sealing device 32, and a locking member 33. The assembly 20 also preferably includes a protective sheath 34 and an anchor 35 for anchoring the assembly 20 to a patient's outer skin surface.

The sleeve 30 preferably comprises a substantially rigid tubular titanium member formed by a peripheral wall 36 (FIG. 4) having an outer surface 37 and an inner surface 38. The inner surface 38 surrounds an interior passageway 39 extending axially from a sleeve first, or proximal, end 40 to a sleeve second, or distal, end 42.

The sleeve 30 is shown mounted on a catheter 22 extending axially through the passageway 39. The catheter outer surface 44 and passageway wall surface 38 are closely dimensioned but with sufficient clearance therebetween to enable the catheter to slide axially and rotate in the passageway 39. The sleeve 30 proximal end 40 is preferably enlarged at 45 to form an interior recess 46 for accommodating the sealing device 32. The sealing device 32 preferably comprises an annular member 48 formed of a soft flexible material, e.g., silicone. The seal member 48 defines an inner peripheral surface 50 surrounding an interior bore 52 which is contiguous with sleeve passageway 39. At least one flexible annular nib 54 extends radially into the bore 52 for contacting and sealing against the catheter outer surface 44.

The enlarged sleeve end 45 has an outer peripheral surface 56 dimensioned to closely fit into bore 58 of anchor 35. The anchor 35 comprises a base portion 60 supporting a ferrule portion 62 which defines the bore 58. The anchor base portion 62 is provided with holes 64 to facilitate the suturing of anchor 35 to the patient's outer skin.

The locking member 33 preferably comprises a split ring formed of soft flexible material, e.g., silicone. More particularly, the locking member 33 is comprised of a peripheral wall 66 having an outer surface 68 and an inner surface 70 surrounding an interior bore 72. The wall 66 is longitudinally split at 74. The wall outer surface 68 is preferably provided with one or more strap pads 71 for securing the locking member 33 to the anchor 35 and/or sleeve 30 using one or more straps 76. The locking member outer wall surface is provided with a proximal annular groove 80 for accommodating suture thread or an appropriately shaped spring clip which can be used by the physician to compress the locking member 33 around the catheter 22. Preferably, a distal annular groove 81 is also provided.

The locking member 33 is configured so that in its natural unlocked state (FIG. 4B), the interior bore 72 is sufficiently large to permit the catheter 22 to slide axially and rotate in the bore 72 and through the sleeve passageway 39. The physician can compress the locking member wall 66 around the catheter to frictionally engage the locking member inner surface 70 against the catheter outer surface 44 to thus lock the catheter outer surface 44 to the sleeve 30 to prevent any relative movement therebetween. This locked state can be maintained by tying suture thread 82 around the locking member wall in grooves 80, 81. Of course, the thread 82 can be readily cut when it is desired to release the locked state to allow the catheter to be repositioned and/or replaced. FIGS. 4D and 4E depict exemplary spring clips 83 which can be alternatively placed in the grooves 80, 81 in lieu of thread 82 for damping the locking member in its locked state.

Figure 12:
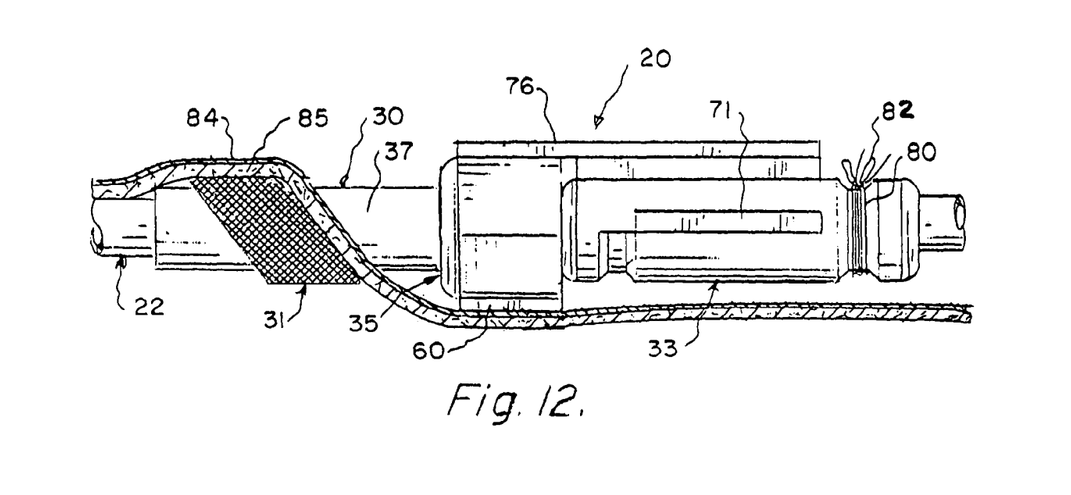
FIG. 12 shows a cross-sectional view of the catheter assembly as implanted with the porous layer positioned subcutaneously adjacent the patient's dermis.

The layer of porous material 31, e.g., titanium mesh, as described in said U.S. application Ser. No. 10/821,383, is mounted around the outer surface 37 of sleeve 30, close to the sleeve distal end 42. In use, it is intended that the sleeve distal end be inserted through an incision 24 in the patient's skin to position the porous layer 31 just below the patient's epidermis skin layer 84 (FIG. 12) and in contact with the patient's dermis layer 85. Note that the porous layer 31 is preferably oriented diagonally with respect to the axis of sleeve 30 to better conform to the patient's skin contour (FIG. 12). This orientation optimizes contact between the porous layer 31 and the patient's dermis to promote, over time, soft tissue ingrowth into the porous layer. This tissue ingrowth acts to firmly anchor the sleeve in place and to form an infection resistant barrier around sleeve 30. This constituentes into the porous layer 31. For example, silver containing compounds and/or antibiotic eluting coatings can be used as antimicrobial agents and steroids can be used as anti-inflammatory agents.

The protective sheath 34 is formed of thin flexible tubular material (e.g., 0.010 wall FEP tubing) and is intended to be mounted around sleeve 30 and porous layer 31 prior to use to avoid injuring the patient's tissue when the sleeve distal end 42 is inserted through the incision 24. As will be further discussed hereinafter, the sheath 34 is removed from the sleeve 30 by the physician after the sleeve and porous layer have been inserted through the incision.

More particularly, the sheath 34 is preferably configured as a substantially tubular, e.g., cylindrical, body 86 having a distal collar 87 and a proximal elongate pull tab 88. An outwardly tapering section 89 extends from the collar 87 to the main body portion 86. Note that the collar 87 and distal portion of section 89 have a diameter smaller than that of the porous layer 31. For example only, the sleeve 30 may have an outer diameter of 0.250 inches, the porous layer 31 an outer diameter of 0.310 inches and the collar 87 an inner diameter of 0.193 inches. An axially oriented score, or perforated line 90 is preformed through the collar 87, the tapering section 89 and the body portion 86 to facilitate the physician peeling the sheath 34 from the sleeve 30. Note in FIG. 4A that the sheath fits tightly around the periphery of sleeve 30 and porous layer 31 and that the tapering section 89 is positioned distally of the porous layer 31. In use, the physician is able to readily peel the sheath from the sleeve with one hand by rolling, or winding, the elongate tab to pull the sheath axially in a proximal direction. Peeling occurs because as the sheath is pulled proximally, the tapering section 89 and collar 87 have to move past the larger diameter porous layer 31 which action causes the sheath to tear along score line 90 allowing it to be easily stripped from the sleeve 30.

In the preferred catheter assembly illustrated in FIGS. 2-4A, the sleeve 30 comprises a rigid titanium tube characterized as follows:

| | |
|---|---|
| overall length | 1.135 inches |
| proximal end 45 length | .250 inches |
| passageway 39 ID | .200 inches |
| end 45 ID | .313 inches |
| sleeve 30 wall thickness | .025 inches |
| porous material 31 OD | .304 inches |
| nib 54 ID | .170 inches |

In an alternative embodiment, the sleeve can be similarly dimensioned but instead of being formed of a rigid material such as titanium, can be formed of a flexible material such as silicone. In such an embodiment, the annular sealing nibs can be integrally formed with the sleeve.

As has previously been mentioned, in use, dermis tissue grows into the porous layer 31 to form a barrier preventing deleterious material from migrating into the patient's body along the sleeve outer surface 37. The aforementioned seal member 48 acts to prevent migration of deleterious material into the body along the narrow gap between the catheter outer surface 44 and the sleeve inner surface 38.

FIGS. 7-12 schematically depict successive steps in an exemplary procedure for implanting the catheter assembly 20 shown in FIGS. 1-6.

Figure 7:
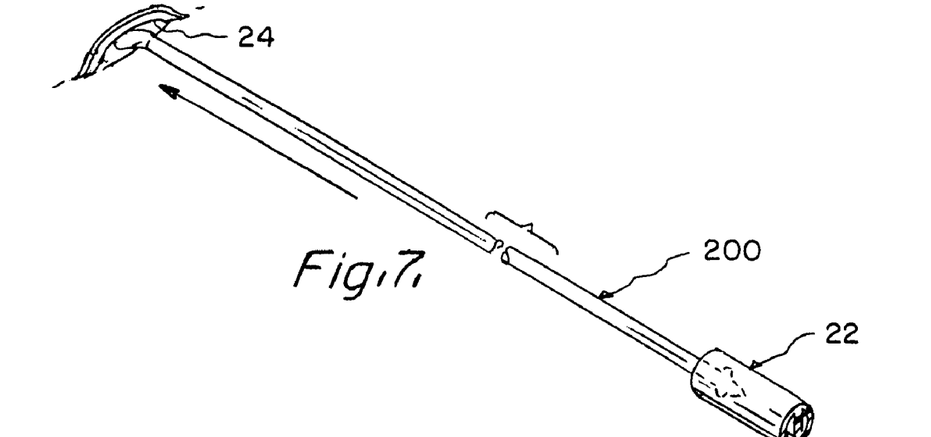
FIGS. 7-11 show successive steps in an exemplary procedure for implanting and utilizing the catheter assembly in accordance with the invention.

FIG. 7 shows the use of a conventional tunneler tool 200 being inserted through a patient's incision 24 to form a tunnel through which the distal end of the catheter 22 is pulled by the proximal end of tool 200.

Figure 8:
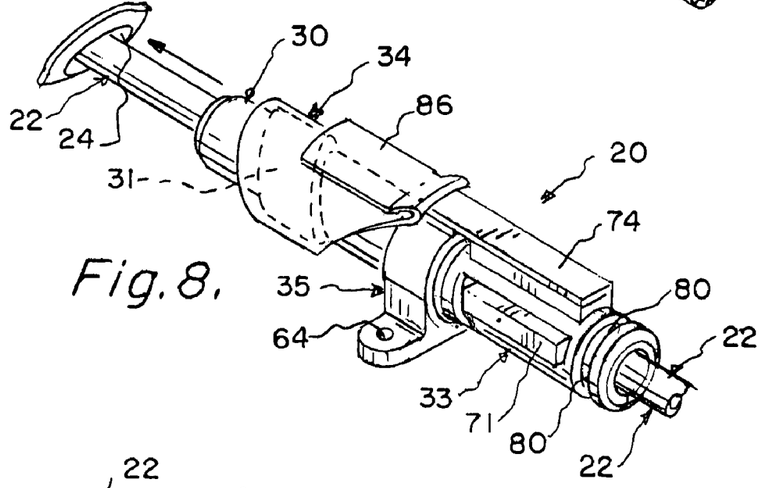

FIG. 8 shows the catheter assembly 20 with the sleeve distal end 42 and protective sheath 34 being inserted through the incision 24.

Figure 9:
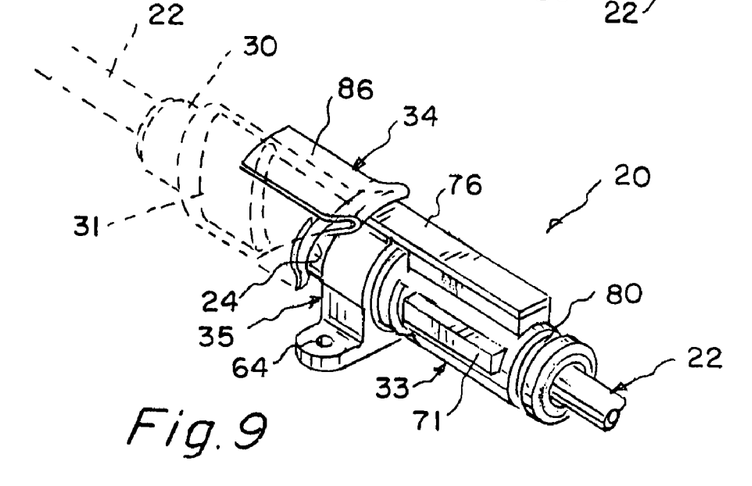

FIG. 9 shows the catheter assembly 20 inserted further into the incision for positioning the porous layer 31 just beneath the epidermal skin layer and adjacent to the dermis layer. Note the protective sheath tab 88 extending outwardly from the sleeve.

Figure 10:
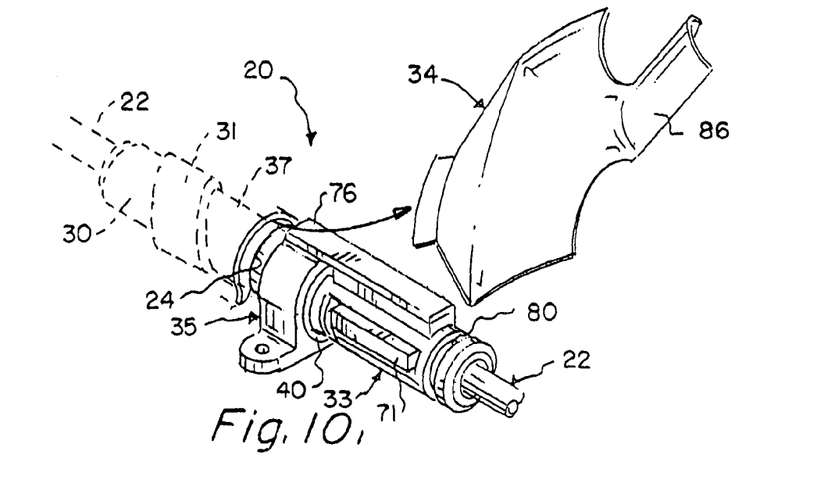

FIG. 10 shows the protective sheath 34 being peeled away (as a consequence of the physician pulling tab 88) from the sleeve 30 to directly expose the porous layer 31 to the patient's dermis.

Figure 11:
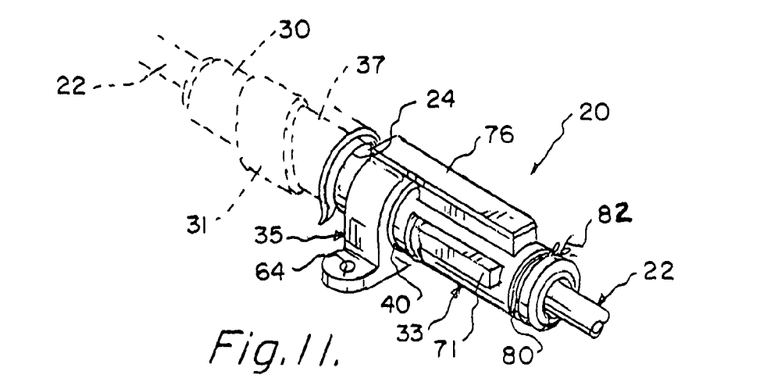

FIG. 11 shows the anchor 35 sutured to the patient's skin to thus securely retain the sleeve proximal end 40 the locking member 33 in place.

FIG. 12 shows a cross-section of the installed catheter assembly 20 with the porous layer 31 contacting the patient's dermis 85 to promote tissue ingrowth.

After initial implantation of the catheter 22 as depicted in FIGS. 7-12, it is sometimes desirable to reposition the catheter for more effective treatment and/or to reduce patient discomfort. Such repositioning can involve slightly adjusting the position and/or orientation of the catheter distal end and is achieved by unlocking the locking member 33 and then sliding the catheter into or out of the sleeve 30 and/or by rotating the catheter in the sleeve.

It is further pointed out that with the locking member 33 in its unlocked state, an implanted catheter can be fully withdrawn through the sleeve proximal end for replacement by a new catheter. Although different technique can be employed, it is contemplated that the physician will thread a guide wire through the old catheter prior to withdrawing it. The new catheter is then threaded along the guide wire and through the sleeve. When the new catheter is properly placed, the guide wire is typically withdrawn.

Figure 13:
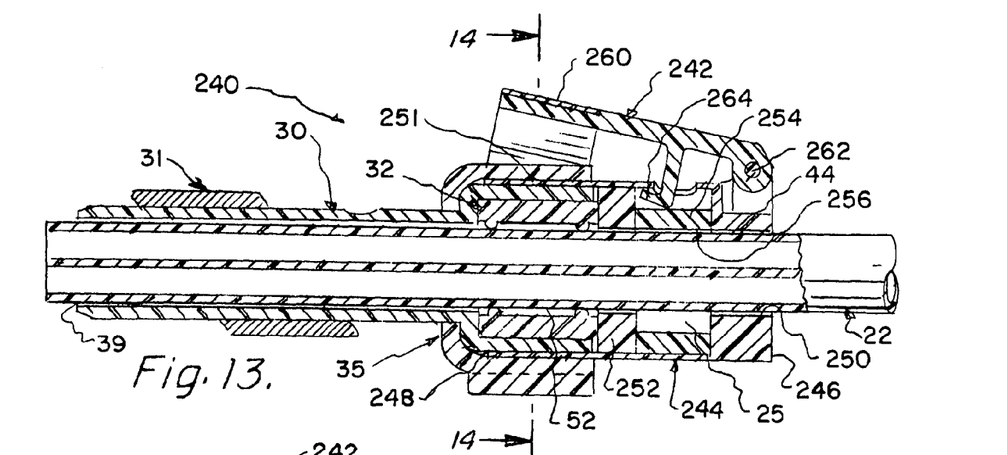
FIG. 13 is a cross sectional view through an alternative catheter assembly embodiment showing its locking member in its unlocked state.
Figure 14:
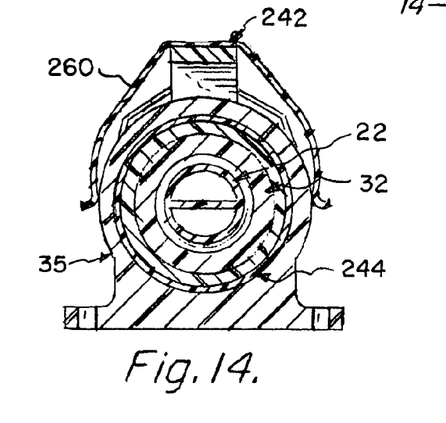
FIG. 14 is a sectional view taken substantially along the plane 14-14 of FIG. 13.
Figure 15:
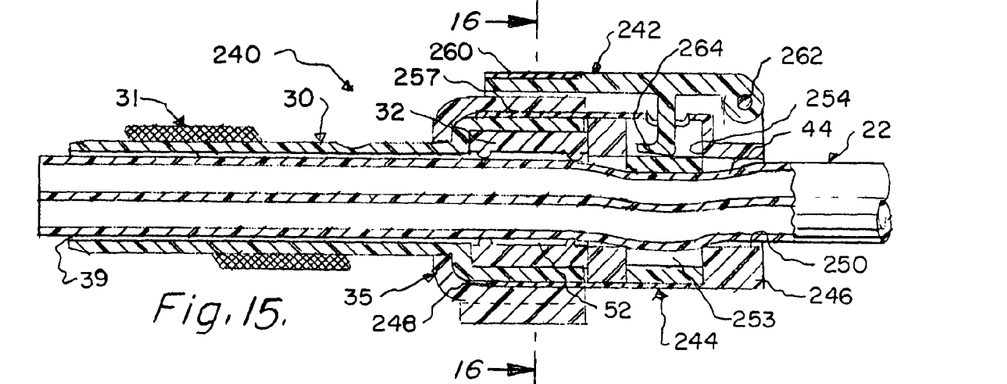
FIG. 15 is a sectional view similar to FIG. 13 showing the locking member in its locked state.
Figure 16:
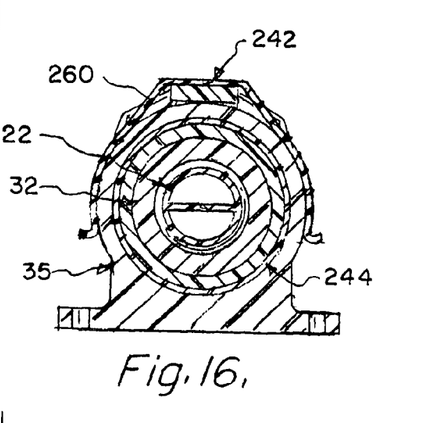
FIG. 16 is a sectional view taken substantially along the plane 16-16 of FIG. 15.

Attention is now directed to FIGS. 13-16 which illustrate a catheter assembly 240 in accordance with the invention employing an alternative locking member 242. FIGS. 13, 14 show the locking member 242 in its unlocked position and FIGS. 15, 16 show the locking member 242 in its locked position. The locking member 242 is comprised of a substantially rigid tubular body 244 having a proximal end 246 and a distal end 248. The proximal end 246 defines a central bore 250 configured to align with the interior bore 52 of seal 32 and passageway 39 of sleeve 30. The distal end 248 of body 244 comprises an enlarged cuff 251 intended to fit around and be secured to the enlarged end of sleeve 30 as shown in FIGS. 13, 14.

An apertured washer 252 is mounted in cuff 251 adjacent to the proximal end of sleeve 30 and spaced from the proximal end 246 of body 244 to define a recess 253 therebetween. A locking element, or ring, 254 is mounted in the recess 253 for movement perpendicular to the axis of body 244. More particularly, the ring 254 is movable between an unlocked position (FIG. 13) where the ring bore 256 is aligned with the bore 250 and a locked position (FIG. 15) where the ring bore 256 is misaligned with bore 250. In the locked position, the ring 254 bears against the outer surface 44 of catheter 22 to prevent catheter movement relative to sleeve 30.

In the exemplary embodiment depicted in FIGS. 13-16, the position of the ring 254 is determined by a manually operable lever 260 hinged at pin 262. The lever 260 carries a projection 264 for bearing against ring 254. When the lever 260 is in its counterclockwise position (FIGS. 15, 16) projection 264 forces ring 254 against the catheter 22 to prevent it from moving relative to sleeve 30. On the other hand, when the lever 260 is moved clockwise to the position shown in FIGS. 13, 14, the force exerted by ring 254 on the catheter is relieved permitting the catheter to rotate and slide axially relative to sleeve 30.

The lever 260 carries a detent mechanism 270 for latching the lever in the locked position of FIG. 15, 16. The exemplary detent mechanism 270 is comprised of arcuate sprint arms 272, 274 which are configured to releasably snap around anchor 276 to latch the lever 260 in the locked position. The locking member 242 can be readily moved to the unlocked position by manually pivoting the lever 260 clockwise to the unlocked position (FIGS. 13, 14).

From the foregoing, it should now be understood that a catheter assembly has been provided particularly configured to facilitate the positioning, repositioning, and/or replacement of a percutaneously implanted catheter. Although only a limited number of structural embodiments have been described, it is recognized that various modifications and alterations will occur to persons skilled in the art which fall within the spirit and intended scope of the invention as defined by the appended claims.

The invention claimed is:

1. A percutaneous catheter assembly including:
    an elongate sleeve comprising a peripheral wall having an outer surface extending from a proximal end to a distal end and an inner surface surrounding an axially extending passageway;
    an elongate conduit comprising a peripheral wall having an outer surface extending from a proximal end to a distal end;
    said elongate conduit extending through said sleeve passageway for axial slidable movement with respect thereto;
    a sealing device in said sleeve for contacting said conduit outer surface to prevent migration of deleterious material between said sleeve inner surface and said conduit outer surface;
    a layer of porous material mounted on said sleeve outer surface close to said sleeve distal end and adapted for subcutaneous placement in contact with a patient's dermis layer to promote tissue ingrowth and form an infection resistant barrier; and
    a locking member retained proximate to said sleeve proximal end, said locking member comprising a longitindinally split ring mounted around said conduit and configured for manual operation to selectively define (1) an unlocked state for permitting axial movement of said conduit through said sleeve passageway and (2) a locked state for frictionally engaging said conduit for preventing axial movement relative to said sleeve passageway.

2. The assembly of claim 1 wherein said sealing device comprises an annular seal defining an interior bore having a flexible annular nib for engaging said conduit outer surface.

3. The assembly of claim 1 wherein said split ring is formed of soft flexible material; and wherein
    said spilt ring in said locked state is radially compressed against said catheter outer surface.

4. The assembly of claim 3 including thread extending around said split ring in said locked state for compressing said split ring around said conduit.

5. The assembly of claim 3 including a spring clip extending around said split ring in said locked state for compressing said split ring around said conduit.

6. The assembly of claim 1 including an anchor configured for external attachment to a patient's outer skin surface; and wherein
    said sleeve proximal end is retained by said anchor.

7. The assembly of claim 6 further including a strap coupling said split ring to said anchor.

8. The assembly of claim 1 further including a protective sheath covering said porous material and configured for ready removal therefrom.

9. The assembly of claim 8 wherein said protective sheath is formed of thin flexible material; and wherein
    said sheath, includes a tab for pulling said sheath from said porous material.

10. The assembly of claim 8 wherein said protective sheath includes a score line.

11. The assembly of claim 1 wherein said layer of porous material incorporates antimicrobial and/or anti-inflammatory agents.

12. The assembly of claim 1 wherein said sleeve is formed of rigid material.

13. The assembly of claims 1 wherein said sleeve is formed of flexible material.

14. An apparatus suitable for percutaneous implantation in a patient's body, said apparatus including:
    an elongate sleeve having first and second ends, said sleeve comprising a wall having a peripheral outer surface and a peripheral inner surface defining a passageway extending axially from said first to said second end;
    an elongate catheter extending through said passageway and configured for axial movement with respect thereto;
    a layer of porous material mounted on said sleeve outer surface proximate to said sleeve second end, said porous material intended for subcutaneous placement in the dermis of a patient's body for promoting tissue ingrowth to form an infection resistant barrier;

an annular seal mounted around said catheter proximate to said sleeve first end; and a locking member retained proximate to said sleeve first end, said locking member comprising a longitindinally split ring mounted around said conduit and configured for manual operation to selectively define (1) an unlocked state for permitting axial movement of said conduit through said sleeve passageway and (2) a locked state for frictionally engaging said conduit for preventing axial movement relative to said sleeve passageway.

15. The apparatus of claim 14 wherein said annular seal includes an annular nib extending radially into said passageway for sealing against the outer surface of said catheter.

16. The apparatus of claim 14 wherein said locking member comprises a split ring for applying a releasable friction force against the outer surface of said catheter.

17. The apparatus of claim 14 further including a protective sheath carried by said sleeve and covering said layer of porous material; and wherein said protective sheath is comprised of thin flexible material configured to be readily removed as said porous material is placed in said dermis.

18. The apparatus of claim 14 wherein said layer of porous material incorporates antimicrobial and/or anti-inflammatory agents.

* * * * *